US007057090B1

(12) United States Patent
Zilinskas et al.

(10) Patent No.: US 7,057,090 B1
(45) Date of Patent: Jun. 6, 2006

(54) AGROBACTERIUM-MEDIATED TRANSFORMATION OF TURFGRASS

(75) Inventors: Barbara A. Zilinskas, Princeton Junction, NJ (US); Lynne H. Pitcher, Highland Park, NJ (US); Subha R. Lakkaraju, East Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/743,840

(22) PCT Filed: Jul. 15, 1999

(86) PCT No.: PCT/US99/16001

§ 371 (c)(1),
(2), (4) Date: Jan. 17, 2001

(87) PCT Pub. No.: WO00/04133

PCT Pub. Date: Jan. 27, 2000

Related U.S. Application Data

(60) Provisional application No. 60/093,163, filed on Jul. 17, 1998.

(51) Int. Cl.
*C12N 15/84* (2006.01)
*C12N 15/29* (2006.01)
*C12N 15/31* (2006.01)
*C12N 15/53* (2006.01)

(52) U.S. Cl. ................ 800/294; 800/279; 800/281; 800/284; 800/288; 800/320; 435/430.1; 435/469

(58) Field of Classification Search ................ 800/320, 800/294, 278; 435/172.1, 172.3, 320.1
See application file for complete search history.

(56) References Cited

U.S. PATENT DOCUMENTS

| 4,810,648 A | * | 3/1989 | Stalker .................... 435/191 |
| 5,591,616 A | | 1/1997 | Hiei et al. |
| 5,731,179 A | | 3/1998 | Komari et al. |
| 5,948,956 A | * | 9/1999 | Lee et al. ................ 800/320 |

FOREIGN PATENT DOCUMENTS

WO    WO 98/06860    2/1998

OTHER PUBLICATIONS (Burch, Ann. Rev. Plant Physiology and Plant Mol Biol, vol. 48, pp. 297-326, 1997.*
Deroles, SC and Gardner, RC; (1998) Plant Molecular Biology 11:355-364.*
Dunwell, JM and Paul, EM, 1990, Outlook on Agriculture 19, 103-109.*
Finnegan J and McElory D Bio/Technology 12:883-888, 1994).*
Potrykus, I. Bio/Technology 8(6):535-542 (Jun. 1990).*
Cheng et al. Plant Physiology 115:971-980 (1997).*
Chawla, H.S. pp. 73-80 and 185-200 In: Plant Biotechnology, A Practical Approach, Science Publishers, Enfield NH (2003).*
Komari, T. Plant Cell Reports 9: 303-306 (1990).*
Aldemita and Hodges, *Agrobacterium tumefaciens*-Mediated Transformation of *japoni* and *indica* Rice Varieties, *Planta, Springer-Verlag* 1996 pp., 612-617.
Belanger et al., Turfgrass Biotechnology, *Rutgers Turfgrass Proceedings*, 28: 1-3 (1996).
Cheng et al., Genetic Transformation of Wheat Mediated by *Agrobacterium tumefaciens*, *Plant Physiol.* (1997) 15:971-980.
Czernilofsky et al., Fate of Selectable Marker DNA Integrated into the Genome of *Nicotiana Tabacum*, DNA, vol. 5, No. 2, 1986, pp. 101-113.
de la Fuente et al., Aluminum Tolerance in Transgenic Plants by Alteration of Citrate Synthesis, *Science*, vol. 276, Jun. 6, 1997, pp. 1566-1568.
Hiei et al., Efficient Transformation of Rice (*Oryza sativa L.*) Mediated by *Agrobacterium* and Sequence Analysis of the Boundaries of the T-DNA, *The Plant Journal* (1994), 6(2), 271-282.
Ishida et al., High Efficiency Transformation of Maize (*Zea mays L.*) Mediated by *Agrobacterium tumefaciens*, *Nature Biotech.*, vol. 14, Jun. 14, 1996, pp. 745-750.
Keller et al., A Plant Homolog of the Neutrophil NADPH Oxidase $gp91^{phox}$ Subunit Gene Encodes a Plasma Membrane Protein with $Ca^{2+}$ Binding Motifs, *The Plant Cell*, vol. 10, 255-266, Feb. 1998.
Komari T., Transformation of Cluttered Cells of *Chenopodium quinoa* by Binding Vectors that Carry a Fragment of DNA from the Virulence Region of pTIBo542, *Plant Cell Reports*, (199) 9:303-306.
Komari et al., Vectors Carrying Two Separate T-DNAs for Co-Transformation of Higher Plants Mediated by *Agrobacterium tumefaciens* and Segregation of Transformants Free from Selection Markers, *The Plant Journal*, (1996) 10(1) 165-174.
Lee L., Turfgrass Biotechnology, *Plant Science*, 15 (1996) 1-8.

(Continued)

*Primary Examiner*—David T. Fox
(74) *Attorney, Agent, or Firm*—Woodcock Washburn LLP

(57) ABSTRACT

A method of obtaining transgenic turfgrass plants by an *Agrobacterium*-mediated transformation protocol is disclosed. The protocol makes use of a modified *Agrobacterium* vector system in which selectable marker genes and other genes of interest are operably linked to strong promoters from monocotyledenous plants, such as actin and ubiquitin promoters, that function efficiently in turfgrass cells. Transgenic turfgrass plants of several species, produced by the *Agrobacterium*-mediated transformation method, are also disclosed.

5 Claims, No Drawings

OTHER PUBLICATIONS

Lodge et al., Broad-Spectrum Virus Resistance in Transgenic Plants Expressing Pokeweed Antiviral Protein, *Proc. Natl. Acad. Sci. USA*, vol. 90, pp. 7089-7093, Aug. 1993.

May et al., Generation of Transgenic Banana (*Musa acuminata*) Plants via *Agrobacterium*-Mediated Transformation, *Biotechnology*, vol. 13, May 1995, pp. 486-492.

Meesters et al., Cloning and Expression of the $\Delta^9$ Fatty Acid Desaturase Gene from *Cryptococcus* curvatus ATCC 20509 Containing Histidine Boxes and a Cytochrome $b_5$ Domain, *Appl. Microbiol. Biotechnol.*, (1997) 47:663-667.

Mittler et al., Coordinated Activation of Programmed Cell Death and Defense Mechanisms in Transgenic Tobacco Plants Expressing a Bacterial Proton Pump, *The Plant Cell*, vol. 7, 29-42, Jan. 1995.

Stukey et al., The *OLE1* Gene of *Saccharomyces cerevisiae* Encodes the $\Delta^9$ Fatty Acid Desaturase and can be Functionally Replaced by the Rat Stearoyl-CoA Desaturase Gene, *The Journal of Biol. Chem.*, vol. 265, No. 33, Nov. 25, 1990, pp. 20144-20149.

Tingay et al., *Agrobacterium tumefaciens*-Mediated Barley Transformation, *The Plant Journal*, (1997) 11(6), 1369-1376.

Wang et al., Expression of the Yeast $\Delta^9$ Desaturase Gene in tomato Enhances its Resistance to Powdery Mildew, *Physiological and Molecular Plant Pathology*, (1998), 52, 371-383.

Wu et al., Disease Resistance Conferred by Expression of a Gene Encoding $H_2O_2$-Generating Glucose Oxidase in Transgenic Potato Plants, *The Plant Cell*, vol. 7, 1357-1368, Sep. 1995.

Zoubenko et al., Plant Resistance to Fungal Infection Induced by Nontoxic Pokeweed Antiviral Protein Mutant, *Nature Biotechnology*, vol. 15, Oct. 1997, pp. 992-996.

Chan, M.-T., et al., "*Agrobacterium*-mediated production of transgenic rice plants expressing a chimeric α-amylase promoter/ β-glucuronidase gene," *Plant molecular Biology*, 1993, 22, 491-506.

Christensen, A.H., et al., "Ubiquitin promoter-based vectors for high-level expression of selectable and/or screenable marker genes in monocotyledonous plants," *Transgenic Res.*, 1996, 5, 213-218.

Dalton, S.J., et al., *Agrobacterium* mediated transformation of *Festuca arundinacea* and *Lolium multiflorum*, *J. of Experimental Botany*, 1998, 49(Suppl.), P4.26, p. 32.

Hiei, Y., et al., "Transformation of rice mediated by *Agrobacterium tumefaciens*," *Plant Molecular Biology*, 1997, 35, 205-218.

Inokuma, C., et al., "Transgenic Japanese lawngrass (Zoysia japonica Steud.) plants regenerated from protoplasts," *Plant Cell Reports*, 1998, 17, 334-338.

Park, H.-D., et al., "Construction of binary vectors for the rice transformation using a rice actin promoter and replication origin of pTi12 isolated from *Agrobacterium tumefaciens* KU12," *J. of Plant Biol.*, 1995, 38(4), 365-371.

Park, S.H., et al., "T-DNA integration into genomic DNA of rice following *Agrobacterium* inoculatin of isolated shoot apices," *Plant Molecular Biology*, 1996, 32, 1135-1148.

Schledzewski, K., et al., "Quantitative transient gene expression: comparison of the promoters for maize polyubiquitin1, rice actin1, maize-derived Emu and CaMV 35S in cells of barley, maize and tobacco," *Transgenic Res.*, 1994, 3, 249-255.

Zhong, H., et al., "Transgenic plants of turfgrass (*Agrostis palustris* Huds) from microprojectile bombardment of embryogenic callus," *Plant Cell Repts.*, 1993, 13, 1-6.

* cited by examiner

AGROBACTERIUM-MEDIATED TRANSFORMATION OF TURFGRASS

This application is a 371 of PCT/US99/16001 filed 15 Jul. 1999, which claims priority to U.S. Provisional Application No. 60/093,163 filed 17 Jul. 1998, the entirety of which is hereby incorporated by reference.

FIELD OF THE INVENTION

This invention relates to the field of plant transformation methods. More specifically, an *Agrobacterium*-mediated method for transforming turfgrass is provided, as well as transgenic turfgrass produced by the method.

BACKGROUND OF THE INVENTION

Various scientific articles and patents are referred to in parentheses throughout the specification. These documents are incorporated by reference herein to describe the state of the art to which this invention pertains. Full citations of the scientific articles appear at the end of the specification.

Turfgrasses and turfgrass breeding are of significant economic importance worldwide. In recent years, traditional breeding programs have been augmented by molecular biological and recombinant techniques. However, similar to most monocotyledenous plants, turfgrasses have proven recalcitrant to tissue culture, transformation and regeneration procedures. Among these, *Agrobacterium*-mediated transformation of a turfgrass heretofore has not been accomplished.

Turfgrass transformation has been achieved using direct methods of DNA transfer, including protoplast transformation and particle gun bombardment. Nonetheless, *Agrobacterium*-mediated transformation offers several advantages over particle gun bombardment or other means of direct gene transfer. These include stable transgene integration without rearrangement of either host or transgene DNA; preferential integration of the transgene into transcriptionally active regions of the genome; ability to transfer large pieces of DNA; and integration of low numbers of gene copies into plant nuclear DNA which is particularly important to minimize possible co-suppression of the transgene in later generations.

Until recently, *Agrobacterium*-mediated transformation was thought to be limited to dicotyledonous plants. However, Hiei et al. in 1994 described efficient transformation of rice by *Agrobacterium*, and subsequently there have been convincing reports for maize, barley and wheat (Ishida et al., 1996; Tingay et al., 1997; Cheng et al., 1997; see also U.S. Pat. No. 5,591,616 to Hiei et al). Numerous factors are of critical importance in *Agrobacterium*-mediated transformation of monocots, including the type and stage of tissue that is infected, the vector and bacterial strains used, plant genotype, tissue culture conditions, and the actual infection process. As a result, methods that have proven successful for *Agrobacterium*-mediated transformation of some monocots, such as rice and maize, have not been successful for transforming turfgrass.

An object of the present invention is to develop an efficient and reliable transformation system for turfgrass, mediated by *Agrobacterium tumefaciens*. Another object of the invention is to regenerate transgenic plants containing one or more foreign genes introduced by *Agrobacterium tumefaciens*-mediated transformation.

SUMMARY OF THE INVENTION

In accordance with the objects of the present invention, an *Agrobacterium*-mediated transformation system for turfgrass is provided, which is efficient and reliable. The invention also provides for the development of transgenic plants containing one or more transgenes of significant practical utility.

According to one aspect of the invention, a method of producing a transgenic turfgrass plant is provided. The method comprises: (a) providing regenerable callus tissue from the turfgrass plant; (b) inoculating the tissue with *Agrobacterium* carrying at least one vector for transformation, the vector comprising virulence genes that confer strong infectivity to *Agrobacterium*, in which vector is inserted a heterologous DNA construct operably linked to a promoter from a monocotylednous species, and a selectable marker gene conferring antibiotic resistance to transformed cells operably linked to a promoter from a monocotyledenous species; (c) culturing the inoculated tissue under conditions that enable the *Agrobacterium* vector to transform cells of the tissue; (d) selectively culturing the inoculated tissue on a selection medium comprising the antibiotic; and (e) regenerating a transformed turfgrass plant from the selectively cultured tissue.

Preferably, the turfgrass is a species selected from the group consisting of creeping bentgrass, tall fescue, velvet bentgrass, perennial ryegrass, hard fescue, Chewings fescue, strong creeping fescue, colonial bentgrass and Kentucky bluegrass. In another preferred embodiment, the *Agrobacterium* comprises a binary vector system and the virulence genes therein are obtained from a plasmid within *Agrobacterium tumefaciens* strain 281. The promoter is preferably selected from the group consisting of maize ubiquitin gene promoters, rice actin gene promoters, maize Adh 1 gene promoters, rice or maize tubulin (Tub A, B or C) gene promoters, and alfalfa His 3 gene promoters. The selectable marker gene preferably confers hygromycin resistance on transformed tissue. The callus used for the transformation preferably is obtained by culturing seeds of the turfgrass on a de-differentiation medium.

Also provided in accordance with another aspect of the invention is a transgenic turfgrass plant prepared by the aforementioned method. Seeds of the transgenic plant are provided as well. In preferred embodiments, the transgenic turfgrass plant comprises a transgene selected from the group consisting of genes encoding glucose oxidase, citrate synthase, Δ-9 desaturase from *Saccharomyces cerevisiae* or *Cryptococcus curvatus*, Δ-11 desaturase, a plant homolog of the neutrophil NADPH oxidase, a bacteriopsin from *Halobacterium halobium*, or pokeweed antiviral protein.

According to another aspect of the invention, a superbinary vector for *Agrobacterium*-mediated transformation of turfgrass is provided. The vector comprises: (a) a virulence region from a Ti plasmid of an *A. tumefaciens* strain that confers to the strain as strong a virulence as that displayed by *A. tumefaciens* strain 281; (b) a selectable marker gene operably linked to a promoter obtained from a gene of a monocotyledenous plant; and (c) a site for insertion of at least one additional coding sequence, operably linked to a promoter obtained from a gene of a monocotyledenous plant, the promoter being the same as or different from the promoter operably linked to the selectable marker gene. In preferred embodiments the virulence region is obtained from *Agrobacterium* strain 281. The promoter is selected from the group consisting of maize ubiquitin gene promoters, rice actin gene promoters, maize Adh 1 gene promoters, rice or maize tubulin (Tub A, B or C) gene promoters, and alfalfa His 3 gene promoters. The selectable marker gene preferably confers hygromycin resistance on transformed cells. The site for insertion of the additional coding sequence preferably comprises a coding sequence of a reporter gene, and/or comprises a coding sequence of a gene encoding the useful proteins listed above.

According to another aspect of the invention, a turfgrass plant cell transformed with the aforementioned *Agrobacterium* vector is provided. Preferably the turfgrass is creeping bentgrass, tall fescue, velvet bentgrass, perennial ryegrass, hard fescue, Chewings fescue, strong creeping fescue, colonial bentgrass or Kentucky bluegrass. A transgenic turfgrass plant regenerated from the aforementioned transformed cell is also provided, as are seeds of the transgenic turfgrass plant.

Other features and advantages of the present invention will be understood by reference to the detailed description and examples that follow.

DETAILED DESCRIPTION OF THE INVENTION

I. Definitions

Various terms used throughout the specification and claims to describe the invention. Unless otherwise specified, these terms are defined as set forth below.

With reference to nucleic acid molecules, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

When used herein in describing components of media or other experimental results, the term "about" means within a margin of commonly acceptable error for the determination being made, using standard methods. For tissue culture media in particular, persons skilled in the art would appreciate that the concentrations of various components initially added to culture media may change somewhat during use of the media, e.g., by evaporation of liquid from the medium or by condensation onto the medium. Moreover, it is understood that the precise concentrations of the macronutrients, vitamins and carbon sources are less critical to the efficacy of the media than are the micronutrient, hormone and antibiotic concentrations.

Nucleic acid sequences and amino acid sequences can be compared using computer programs that align the similar sequences of the nucleic or amino acids thus define the differences. In the comparisons made in the present invention, the CLUSTLW program and parameters employed therein were utilized (Thompson et al., 1994, supra). However, equivalent alignments and similarity/identity assessments can be obtained through the use of any standard alignment software. For instance, the BLAST programs used to query sequence similarity in GenBank and other public databases may be used. The GCG Wisconsin Package version 9.1, available from the Genetics Computer Group in Madison, Wis., and the default parameters used (gap creation penalty=12, gap extension penalty=4) by that program may also be used to compare sequence identity and similarity.

The term "substantially the same" refers to nucleic acid or amino acid sequences having sequence variations that do not materially affect the functionality of cis acting regulatory sequences (e.g, promoters, transcriptional response elements, etc.) or the nature of the encoded gene product (i.e. the structure, stability characteristics, substrate specificity and/or biological activity of the protein). With particular reference to nucleic acid sequences, the term "substantially the same" is intended to refer to conserved sequences governing expression and to the coding region (referring primarily to degenerate codons encoding the same amino acid, or alternate codons encoding conservative substitute amino acids in the encoded polypeptide).

The terms "percent identical" and "percent similar" are also used herein in comparisons among nucleic acid sequences. When referring to nucleic acid molecules, "percent identical" refers to the percent of the nucleotides of the subject nucleic acid sequence that have been matched to identical nucleotides by a sequence analysis program. When referring to amino acid sequences, "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205).

With respect to oligonucleotides or other single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "coding sequence" or "coding region" refers to a nucleic acid molecule having sequence information necessary to produce a gene product, when the sequence is expressed.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e.g. enhancers) in an expression vector.

When describing the organization of a nucleic acid molecule, the term "upstream" refers to the 5' direction and the term "downstream" refers to the 3' direction.

The term "reporter gene" refers to a nucleic acid coding sequence that encodes a readily detectable gene product, which may be operably linked to a promoter region to form a chimeric gene, such that expression of the coding sequence is regulated by the promoter and the product of the coding sequence is readily assayed.

The term "selectable marker gene" refers to a gene that when expressed confers a selectable phenotype, such as antibiotic resistance, on a transformed cell or plant.

Transcriptional and translational control sequences, sometimes referred to herein as "expression control" sequences or elements, or "expression regulating" sequences or elements, are DNA regulatory elements such as promoters, enhancers, ribosome binding sites, polyadenylation signals, terminators, and the like, that provide for the expression of a coding sequence in a host cell. The term "expression" is intended to include transcription of DNA and translation of the mRNA transcript.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" refers to genetic sequence used to transform plant cells and generate progeny transgenic plants. At minimum a DNA construct comprises a coding region for a selected gene product, operably linked to 5' and 3' regulatory sequences for expression in transformed plants. In preferred embodiments, such constructs are chimeric, i.e., the coding sequence is from a different source one or more of the regulatory sequences (e.g., coding sequence from tobacco and promoter from maize). However, non-chimeric DNA constructs also can be used. In addition to methods specifically described herein, the transforming DNA may be prepared according to standard protocols such as those set forth in Ausubel et al. (1999). A plant species or cultivar may be transformed with a DNA construct (chimeric or non-chimeric) that encodes a polypeptide from a different plant species or cultivar, or a non-plant species. Alternatively, a plant species or cultivar may be transformed with a DNA construct (chimeric or non-chimeric) that encodes a polypeptide from the same plant species or cultivar. The term "transgene" is sometimes used to refer to the DNA construct within the transformed cell or plant.

A cell has been "transformed" or "transfected" by a DNA construct when such DNA has been introduced inside the cell. The transforming DNA may or may not be integrated (covalently linked) into the genome of the cell. For example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

II. Description

The present invention provides an efficient and reliable transformation system for turfgrass species. The species chosen to develop this system uses creeping bentgrass, *Agrostis palustris* Huds. Due to the reasonably close similarity among various turfgrasses (i.e., in physiology, genome organization, etc.), this transformation system will have broad applicability to many different kinds of turfgrass. For instance, the system also has been applied to velvet bentgrass, *Agrostis canina* L. and tall fescue, *Festuca arundinacea* Scheb., and although the transformation efficiency is not as great as for creeping bentgrass, it is clear that transformants can be obtained from several species. Other turfgrasses contemplated for the transformation system of the invention include, but are not limited to, perennial ryegrass, hard fescue, Chewings fescue, strong creeping fescue, colonial bentgrass and Kentucky bluegrass.

Binary vectors are commonly used in *Agrobacterium*-mediated transformation. Recently, a "superbinary" vector system was developed (Komari et al., 1990; Saito et al., 1992; Hiei et al., 1994; U.S. Pat. No. 5,731,139 to Komari et al.). In this system the plasmid that carries the T-DNA also contains certain virulence genes from strain A281, which is known for high efficiency of transformation.

In arriving at the present invention, the conditions and vectors described for transformation of rice (Hiei er al., 1994) and maize (Ishida et al., 1996) were initially used, but without success in creeping bentgrass. It was suspected that a major problem with these vectors was the CaMV35S promoter which drives the expression of the selectable marker in the rice and maize systems. Therefore, a new vector was constructed, which has the components of the "superbinary vector" developed by Hiei et al. (1994), coupled with a suitable selectable marker (hygromycin resistance) and the easily scorable β-glucuronidase (GUS) reporter gene. More significantly, in the new vector, the expression of each of these respective transgenes is driven by promoters for strong, constitutive expression in monocots, e.g., the rice actin and maize ubiquitin promoters. Independent transformations, conducted over the course of several months, demonstrated that an *Agrobacterium tumefaciens* such as this can indeed transfer DNA into the chromosomes of various turfgrasses.

Certain features of the *Agrobacterium*-mediated turfgrass transformation system describe herein are believed to be particularly important for successful transformation and regeneration of transgenic turfgrass. One of these is the use of Ti plasmids from strongly infective *Agrobacterium* strains. Preferred for use are superbinary hybrid *Agrobacterium* vectors, such as pSB1 and pSB11 (Komari et al., 1996). These and other superbinary vectors that can be modified for use in the present invention are described in U.S. Pat. No. 5,731,179 to Komari et al. These vectors contain a DNA region containing virB gene and virG gene in virulence region of Ti plasmid pTiBo542 of *Agrobacterium tumefaciens*, which is a Ti plasmid contained in *A. tumefaciens* strain A281 (ATCC Accession No. 37349), a strain known for its strong virulence. The virB and virG genes in the virulence region of pTiBo542 are contained a 15.2 kb KpnI restriction fragment, which itself may be used in the present invention. Moreover, although vectors comprising the hypervirulence-conferring portions of pTiBo542 are exemplified herein, it will be appreciated by persons skilled in the art that corresponding genes from any highly virulent *Agrobacterium* strain may be used instead. These include strains that are presently available as well as strains that may be discovered in the future.

A particularly important feature of the invention is the modification of *Agrobacterium* vectors to contain promoters and other regulatory sequences particularly suited for expression in turfgrasses. Thus, the strong constitutive promoters from the rice actin gene and the maize ubiquitin gene are exemplified herein. However, any constitutively expressed or inducible promoter for expression in monocots may be used in the present invention. Examples of other constitutive promoters suitable for use in the present invention are the maize Adh 1 promoter, the rice or maize tubulin (Tub A, B or C) promoters, and the alfalfa His 3 promoter. Monocotyledenous tissue-specific promoters also may be utilized. For example, seed-specific promoters suitable for use in the present invention include zein promoters, such as the 27-kDa zein promoter or the 10-kDa zein promoter.

The choice of selectable marker is also important. Hygromycin is exemplified herein as a selectable marker. However, other selectable markers are also suitable for use in the invention. For instance, resistance to phosphothricin herbicides is particularly useful for selecting transformed monocotyledenous plant cells. In addition, kanamycin is routinely used as a selection medium for plant transformation, though it is less preferred for use in the present invention than is hygromycin.

For *Agrobacterium*-mediated transformation, an antibiotic to eliminate *Agrobacterium* is included in the selection medium. Cefotaxime is the preferred antibiotic for this purpose. However, Augmentin (amoxicillin and lithium clavulenate) and carbenincillin also have been found effective for eliminating *Agrobacterium*.

If a reporter gene is utilized, it can be any one of several commonly used in the art. Examples of suitable reporter genes include, but are not limited to, genes encoding β-glucuronidase (GUS), luciferase, chloramphenicol acetyl transferase (CAT), green fluorescent protein (GFP) and modified forms of GFP (e.g., EGFP, EPFP and $GFP_{UV}$.

In addition, the use of friable, regenerable callus for the transformation protocol is considered particularly important to successful, efficient transformation and regeneration of intact plants. In a preferred embodiment, the callus is generated from embryogenic tissue, most preferably mature seeds, though it may also be generated from seed parts or immature seeds. Other organogenic tissues may also be utilized as starting material for callus growth. It has been found in accordance with the present invention that the culture media described herein will facilitate the growth of appropriate (i.e. friable, regenerable) callus tissue, which is best harvested as soon as a sufficient amount of callus is generated from the starting material.

To optimize the conditions for efficient transformation of turfgrass, a number of parameters may be systematically altered to determine the best conditions to achieve efficient and easily reproducible transformation. Conditions that may be altered include: 1) the culture medium and induction agents immediately prior to and during co-cultivation with *Agrobacterium*; 2) inoculation and co-culture methods and time period; 3) the presence and absence of surfactants in the inoculation medium; and 4) use of embryogenic callus versus suspension cell cultures. Optimum conditions have been established for creeping bentgrass. Modifications of these conditions have enabled the transformation of callus obtained from velvet bentgrass and tall fescue.

Thus, the present invention provides a method for generating transgenic turfgrass using *Agrobacterium* vectors, that heretofore has been unavailable. A preferred embodiment of the present invention comprises the following transformation/regeneration protocol, based on *Agrobacterium*-mediated transformation.

1) The starting tissue (e.g., mature seeds in a particularly preferred embodiment) of the selected turfgrass are surface-sterilized and placed on a standard de-differentiation tissue culture medium (see the examples) for about 3–6 weeks, preferably in the dark, at room temperature.

2) Proliferating calli are selected and transferred to fresh medium of the same type on a regular basis. Only callus that is friable and regenerable should be selected for further culture.

3) Prior to exposure to *Agrobacterium*, the chosen callus is transferred to new medium to promote active cell division; the callus is used for transformation within about a week of the final transfer to fresh medium.

4) The *Agrobacterium* strain carrying the transforming plasmids is grown, induced with acetosyringone (a phenolic compound demonstrated to induce *Agrobacterium* vir gene expression) and resuspended in an inoculation medium comprising acetosyringone and, optionally, a surfactant such as pluronic F-68 or another suitable surfactant.

5) Optionally, callus may be pre-treated prior to inoculation with *Agrobacterium* by vacuum-infiltration with inoculation medium containing acetosyringone.

6) The callus tissue is then placed in the presence of the *Agrobacterium* suspension to allow the bacteria to infiltrate the callus tissue. Optionally, excess *Agrobacterium* may thereafter be removed from the calli by gentle vacuum filtration. Calli, on a sterile filter, are then placed on co-cultivation solid medium (standard de-differentiation medium but containing glucose and acetosyringone). Co-cultivation of the calli with the *Agrobacterium* cells that remain associated with the calli is allowed to proceed for a few (e.g., three) days, the object being to allow sufficient time for penetration of the T-DNA into the plant cells while avoiding overgrowth of the calli with the *Agrobacterium*.

7) The calli are then transferred to selection medium containing the selection antibiotic (e.g., hygromycin) and the antibiotic for removal of the *Agrobacterium*. Calli are kept on this medium for several weeks (e.g. 6–8 weeks) and checked periodically for proliferation of the calli on the selection medium.

8) New growth that appears on calli on the selection medium is first transferred to fresh selection medium and allowed to proliferate. This first selection is best performed when the new growth is as small as possible in order to ensure that independent transformants are selected and proliferated in the absence of other independent transformants.

9) After sufficient proliferation, a small portion of each of the putatively transformed calli is tested for expression of the gene of interest, and/or for expression of a detectable marker gene (e.g., GUS activity). The remaining portions of positive-testing calli are retained on the selection medium for continued subculture and proliferation. Subsequently, the transformed calli are transferred to a regeneration medium containing growth regulators to promote shoot differentiation.

10) When sufficiently developed, the shoots are transferred to a second regeneration medium formulated to further stimulate root growth. After a sufficient growth phase, plantlets are transferred to either new tissue culture medium or to soil or equivalent planting media.

This invention provides transgenic turfgrass produced by the above-described methods, and also is intended to encompass cells and tissues of those plants, including, but not limited to, leaves, stems, shoots, roots, flowers, fruits and seeds. In a preferred embodiment, seeds of the transgenic plants produced by the methods of the invention are provided.

The plants grown from the aforementioned seeds, or seeds from other turfgrass species or varieties, or the progeny thereof, all of which are considered within the scope of this invention, are used in crosses and selection methods to transfer genes of interest into other turfgrass genotypes, cultivars, varieties and the like.

Plants grown from transgenic turfgrass seeds can also be used to detect the presence of the inserted transgene and vector sequences using DNA extraction, cleavage by one or more restriction endonucleases, and analysis, e.g., Southern blotting using probes derived from the gene or genes of interest. In this manner, the transfer of foreign genes into progeny of breeding crosses can be monitored.

The *Agrobacterium*-mediated turfgrass transformation system of the present invention can be used to introduce many genes of interest into different turfgrass species or varieties. Accordingly, the present invention provides several specific hybrid vectors for *Agrobacterium*-mediated transformation of turfgrass. A number of gene constructs are of considerable practical utility as used to create one or more different transgenic turfgrasses. These include: 1) the gene encoding glucose oxidase from *Aspergillus niger* which when expressed in potato provides resistance to bacterial and fungal pathogens through its production of $H_2O_2$ in the plant apoplast (Wu et al., 1995); 2) the gene encoding citrate synthase from *Pseudomonas aeruginosa* which when expressed in the cytoplasm of tobacco provides tolerance to toxic levels of aluminum in the soil (Manuel et al., 1997); 3) the genes encoding Δ-9 desaturase from *Saccharomyces cerevisiae* (Stukey et al., 1990) and *Cryptococcus curvatus* (Meesters et al., 1997) and Δ-11 desaturase from *Trichoplosia ni* (Knipple et al., 1998). When the ole1 gene from yeast was expressed in tomato and eggplant, it provided resistance to fungal pathogens (Wang et al., 1998); 4) the recently identified gene encoding a plant homolog of the neutrophil NADPH oxidase which is though to be responsible for the oxidative burst which is critical in plant defense against pathogens (Keller et al., 1998); 5) the gene encoding bacteriopsin, a proton pump from the bacterium, *Halobacterium halobium*, which has been demonstrated to protect transgenic tobacco expressing the protein against plant pathogens (Mittler et al., 1995); and 6) the gene encoding pokeweed antiviral protein, which is a ribosome-inactivating protein from the plant *Phytolacca americana*; expression of this gene in tobacco provides resistance to viral and fungal pathogens (Lodge et al., 1993; Zoubenko et al., 1997).

The following examples are provided to describe the invention in greater detail. They are intended to illustrate, not to limit, the invention.

EXAMPLE 1

Construction of *Agrobacterium tumefaciens* Strain LBA4404, Containing pSB111SH Superbinary Hybrid Vector The vector pTOK233 described by Hiei et al. (1994) for transformation of rice was not useful for transformation of creeping bentgrass despite numerous attempts. It was suspected that the cauliflower mosaic 35S promoter was the source of the problem in that it appears to be a very weak promoter in turfgrass. Accordingly, an alternate pair of plasmid vectors was obtained, namely pSB1 and pSB11 (Japan Tobacco, Inc. Plant Breeding and Genetics Research Laboratory, 700 Higashibara, Toyoda, Iwata, Shizuoka, Japan). pSB11 is a 6.3 kb plasmid which contains a multi-cloning region with a number of unique restriction sites between the left and right border sequences delineating the T-DNA region that will be transferred from *Agrobacterium tumefaciens* to the plant genome. Monocot "expression cassettes" expressing hygromycin B phosphotransferase (to confer hygromycin resistance) and β-glucuronidase (GUS, as a scorable reporter) were inserted into pSB11 into the multiple cloning region between the T-DNA border sequences. The following strategy was used.

First, plasmid pAcH1 (provided by Dr. German Spangenberg) was partially digested with Sac I which yielded several restriction fragments, of which the 2645 bp fragment was gel-purified. This fragment contains a 3' modified hph coding sequence (conferring hygromycin resistance) cloned inframe and downstream from the Act 1 5' promoter sequence, first exon (non-coding), first intron and a portion of the second, ATG-containing exon of the gene. Transcription termination signals are provided by the CaMV35S terminator. This 2645 bp fragment was cloned into the unique Sac I restriction site between the right and left border sequences of plasmid pSB11. This plasmid was named pSB11S. Next, a 4175 bp Hind III fragment was excised from plasmid pAHC25, kindly provided by Dr. Peter Quail. This fragment contains the promoter, 5' untranslated exon, and first intron of the maize ubiquitin (Ubi1) gene fused with the GUS reporter gene coding sequence (derived form pBI101.2). This Hind III restriction fragment was cloned into the unique Hind III site of pSB11S, between the right and left border sequences of the plasmid. The resultant plasmid was named pSB11SH.

Next, this intermediate vector (pSB11SH) was electroporated into *Agrobacterium tumefaciens* LBA4404 containing the "acceptor vector" pSB1. Plasmid pSB1 is a "superbinary vector" which carries a 15.2 kb Kpn I fragment containing additional copies of the vir B, vir C and vir G virulence genes to enable efficient T-DNA transfer to monocots. Following homologous recombination between the "acceptor vector" and the "intermediate vector", a co-integrate "hybrid vector" was obtained. Bacteria expressing the drug resistance markers derived from both the acceptor and intermediate vectors were selected on AB plates containing 10 μg/ml tetracycline and 50 μg/ml spectinomycin, and the resultant strains carrying the "hybrid vector" were used in plant transformations.

EXAMPLE 2

Agrobacterium-Mediated Transformation of Creeping Bentgrass with Superbinary Hybrid Vector pSB111SH In this example, an *Agrobacterium* transformation system for creeping bentgrass, *Agrostis palustris*, is described, which utilizes the superbinary hybrid test vector described in Example 1.

Media:

MMSG Medium

Per Liter:

| | |
|---|---|
| Murashige and Skoog basal salts | 4.33 g |
| sucrose | 30 g |
| Gamborg vitamins (1000×) | 1 ml |
| casein hydrolysate | 500 mg |
| dicamba (dichloro-o-anisic acid) | 6.6 mg |
| 6 BAP (6-benzylaminopurine) | 0.5 mg |
| Adjust the pH to 5.6 to 5.8. | |
| Add GEL-GRO ™* | 2.4 g |
| Autoclave and dispense into Petri dishes. | |

(*GEL-GRO ™ is gellan gum, an agar substitute, manufactured by ICN Biomedicals, Inc. If GEL-GRO ™ is unavailable, agar or an equivalent agar substitute may be utilized.)

Modified AAM Medium

Per Liter:

| | |
|---|---|
| glutamine | 875 mg |
| aspartic acid | 266 mg |
| arginine | 174 mg |
| glycine | 7.5 mg |
| sucrose | 88.5 mg |
| 2,4-D | 1 mg |
| kinetin | 0.2 mg |
| $GA_3$ | 0.1 mg |
| Murashige & Skoog vitamins (1000×) | 1 ml |
| casamino acids | 500 mg |
| glucose | 36 g |
| Adjust pH to 5.2 and autoclave. | |
| Add acetosyringone to a final concentration of 100 μM. | |

Regeneration Medium MSO I

Per Liter:

| | |
|---|---|
| Murashige & Skoog basal salts | 4.33 g |
| Gamborg vitamins (1000×) | 1 ml |
| sucrose | 30 g |
| myo-inositol | 100 mg |
| 6-benzylaminopurine | 1 mg |
| Adjust pH to 5.8. | |
| Add GEL-GRO ™ | 2.4 g |
| Autoclave and dispense into plates. | |

Regeneration Medium MSO II

Per Liter:

| | |
|---|---|
| Murashige & Skoog basal salts | 4.33 g |
| Gamborg vitamins (1000×) | 1 ml |
| sucrose | 30 g |
| myo-inositol | 100 mg |
| Adjust pH to 5.8. | |
| Add GEL-GRO ™ | 2.4 g |
| Autoclave and dispense into petri dishes and plantcons. | |

AB medium

1. Prepare a stock of AB Buffer at 20× and autoclave:

Per Liter:

| | |
    |---|---|
    | $K_2HPO_4$ | 60 g |
    | $NaH_2PO_4$ | 20 g |

2. Prepare a stock of AB Salts at 20× and autoclave:

Per Liter:

| | |
    |---|---|
    | $NH_4Cl$ | 20 g |
    | $MgSO_4.7H_2O$ | 6 g |
    | KCl | 3 g |
    | $CaCl_2$ | 0.2 g |
    | $FeSO_4.7H_2O$ | 50 mg |

3. For 1 liter of medium for plates:

Mix 5 g of glucose, 15 g of agar, and 900 ml of $H_2O$ and autoclave.
    Add 50 ml of the 20× stock of AB Buffer and 50 ml of the 20× stock of AB Salts.
    Add 10 mg tetracycline and 50 mg spectinomycin.
    Pour into petri dishes.

Production of regenerable callus: Mature seeds of creeping bentgrass (Crenshaw cultivar) were surface-sterilized and plated on MMSG medium. The plates were kept in the dark at room temperature for 3–6 weeks. The proliferating calli were selected and transferred to new MMSG medium on a regular basis. Only callus that was friable and regenerable was used for transformation. The chosen callus was transferred to new MMSG medium prior to co-cultivation to promote active cell division and was used for transformation within a week after transferring to new plates. The nature of the callus (i.e., friability, regenerability and active growth) is believed to play a key role in obtaining efficient transformation.

Induction of *Agrobacterium tumefaciens* with acetosyringone: *Agrobacterium tumefaciens* LBA4404, harboring vector pSB111SH, was streaked from a glycerol stock stored at −80° C. and grown at 28° C. on plates containing AB medium, supplemented with 10 μg/ml tetracycline and 50 μg/ml spectinomycin. After three to six days, the cells were scraped from the plate and suspended in modified AAM medium containing 100 μM acetosyringone to an $OD_{660}$ of approximately 0.5. The bacterial suspension was left at 25° C. in the dark with shaking for 3.5 hours before using it for co-cultivation.

Co-cultivation: A given amount of friable callus was mixed with the pre-induced *Agrobacterium* suspension and incubated at room temperature in the dark for 1.5 hours. Then the contents were poured into a sterile Buchner-funnel containing a sterile Whatman filter paper. Mild vacuum was applied to drain the excess *Agrobacterium* suspension. Then, the filter was moved to a plate containing MMSG medium supplemented with 100 μM acetosyringone, and the plate was stored in the dark at room temperature for three days.

Selection and regeneration of transformants: Subsequent to the three day co-cultivation, the co-cultivated calli were rinsed with 250 μg/ml cefotaxime to suppress bacterial growth, and the calli were placed on agar plates containing MMSG medium containing 200 μg/ml hygromycin and 250 μg/ml cefotaxime. The calli were kept in the dark at room temperature for 6–8 weeks and checked periodically for proliferation of the calli on hygromycin.

Subsequently, the hygromycin-resistant calli were placed on regeneration medium containing hygromycin and cefotaxime. The proliferating calli were first moved to Regeneration Medium I (MSO I) containing cefotaxime and hygromycin. These calli were kept in the dark at room temperature for a week and were then moved to light for approximately two weeks. The tiny plants were separated and transferred to deep petri plates containing Regeneration Medium II (MSO II) to promote root growth. Hygromycin and cefotaxime were included in the medium to respectively maintain selection pressure and kill any remaining *Agrobacterium* cells. After 2–3 weeks, or when the plants were 1.5–2 cm tall, they were moved to plantcons containing MSO II without antibiotics. When the plants were ~10 cm tall and had developed extensive root systems, they were transferred to soil and grown in the laboratory for 3–4 weeks with 12 hours light/day. The plants were transferred to 6" pots to the greenhouse, where the temperature was maintained between 21°–25° C. Supplemental lighting added approximately 50 $\mu m^{-2}$ $sec^{-1}$ at canopy level when natural light was low and provided a minimal light period of 14 hours.

In connection with the transformation of creeping bentgrass, it should be noted that the media and protocols described below in Examples 3 and 4 may also be used to successfully transform and regenerate creeping bentgrass.

EXAMPLE 3

*Agrobacterium*-Mediated Transformation of Tall Fescue with Superbinary Hybrid Vector PSB111SH In this example, an *Agrobacterium* transformation system for tall fescue, *Festuca arundinacea* Scheb., is described, which utilizes the superbinary hybrid test vector described in Example 1.

Media:

MMSG Medium

This medium was formulated as described in Example 2.

Inoculation Medium

Per Liter:

| | |
|---|---|
| Murashige & Skoog basal salts | 440 mg |
| sucrose | 30 g |
| dicamba | 6.6 mg |
| 6 BAP (6-benzyl aminopurine) | 0.5 mg |
| Gamborg vitamins (1000×) | 1 ml |
| casein hydrolysate | 500 mg |
| glucose | 10 g |

Adjust pH to 5.7 and autoclave.
Immediately before use add acetosyringone to a final

Inoculation Medium

Per Liter:

concentration of 200 μM and pluronic F-68 to a final concentration of 0.02%.

Co-Cultivation Medium

Per Liter:

| | |
|---|---|
| Murashige and Skoog basal salts | 4.4 g |
| sucrose | 30 g |
| glucose | 10 g |
| Gamborg vitamins (1000×) | 1 ml |
| casein hydrolysate | 500 mg |
| dicamba (dichloro-o-anisic acid) | 6.6 mg |
| 6 BAP (6-benzylaminopurine) | 0.5 mg |
| Adjust the pH to 5.7 | |
| Add GEL-GRO ™ | 2.4 g |
| Autoclave | |
| Add acetosyringone | 39.2 mg |

Regeneration Medium MSO I

This medium was formulated and prepared as described in Example 2.

Regeneration Medium MSO II

This medium was formulated and prepared as described in Example 2.

AB Medium

This medium was formulated and prepared as described in Example 2.

Production of regenerable callus: Mature seeds of tall fescue were surface-sterilized and plated on MMSG medium. The plates were kept in the dark at room temperature for 3–6 weeks. The proliferating calli were selected and transferred to new MMSG medium on a regular basis. Callus chosen for transformation was transferred to new MMSG medium prior to co-cultivation to promote active cell division. The nature of the callus (i.e., friability, regenerability and active growth) is believed to play a key role in obtaining efficient transformation.

Preparation of *Agrobacterium tumefaciens* suspension: *Agrobacterium tumefaciens* LBA4404, harboring vector pSB111SH, was streaked from a glycerol stock stored at −80° C. and grown at 28° C. on plates containing AB medium, supplemented with 10 μg/ml tetracycline and 50 μg/ml spectinomycin. After three to six days, the cells were scraped from the plate and suspended in inoculation medium containing 200 μM acetosyringone and 0.02% pluronic F-68 to an $OD_{660}$ between 0.5 and 0.8.

Co-cultivation of callus with *Agrobacterium*: The friable callus chosen for transformation was placed in a sterile tube and mixed with 30 ml of *Agrobacterium* suspension. The tube was capped and covered with aluminum foil, and the contents were mixed by inversion and gently shaken for about 1.5 hr. The contents of the tube were poured into a Buchner funnel, fitted with Whatman filter. Mild vacuum was applied to flask. The filter disks containing callus with

*Agrobacterium* were moved to co-cultivation plates containing acetosyringone (200 μM) and glucose at 10 g/l. The plates were sealed with parafilm and placed in the dark at room temperature for three days.

Selection and regeneration of transformants: Subsequent to the three day co-cultivation, the co-cultivated calli were rinsed with 250 μg/ml cefotaxime solution to suppress bacterial growth, and the calli were placed on MMSG medium containing 200 μg/ml hygromycin and 250 μg/ml cefotaxime. The calli were kept in the dark at room temperature for 6–8 weeks and checked periodically for proliferation of the calli on hygromycin. The hygromycin-resistant calli were moved to new MMSG plates with hygromycin and kept in the dark at room temperature until well proliferated. Then a portion of the hygromycin-resistant callus was tested for GUS activity to ensure that transformation had occurred.

Portions of the putatively transformed calli were then moved to Regeneration Medium I (MSO I) containing cefotaxime and hygromycin and kept in the dark room at room temperature for a week and were subsequently moved to the light for regeneration. The tiny shoots were separated and transferred to deep petri plates containing Regeneration Medium II (MSO II) to promote root growth and hygromycin and cefotaxime to maintain respectively selection of the transformants and kill any remaining *Agrobacterium*.

EXAMPLE 4

*Agrobacterium*-Mediated Transformation of Velvet Bentgrass with Superbinary Hybrid Vector pSB111SH In this example, an *Agrobacterium* transformation system for velvet bentgrass, *Agrostis canina* L., is described, which utilizes the superbinary hybrid test vector described in Example 1.

Media: All media were formulated and prepared as described in Example 3.

Production of regenerable callus: Mature seeds of velvet bentgrass were surface-sterilized and plated on MMSG medium. The plates were kept in the dark at room temperature for 3–6 weeks. The proliferating calli were selected and transferred to new MMSG medium on a regular basis. Callus chosen for transformation was transferred to new MMSG medium prior to co-cultivation to promote active cell division The nature of the callus (i.e., friability, regenerability and active growth) is believed to play a key role in obtaining efficient transformation.

Preparation of *Agrobacterium tumefaciens* suspension: *Agrobacterium tumefaciens* LBA4404, harboring vector pSB111SH, was streaked from a glycerol stock stored at −80° C. and grown at 28° C. on plates containing AB medium, supplemented with 10 μg/ml tetracycline and 50 μg/ml spectinomycin. After three to six days, the bacterial lawn was scraped from one (82 mm diameter) plate and suspended in 6 ml inoculation medium containing 200 μM acetosyringone. The bacterial suspension was left at 28° C. in the dark with shaking overnight. In the morning acetosyringone was added to a final concentration of 400 μM and pluronic F-68 to 0.02%.

Co-cultivation: A sterile filter was placed on a co-cultivation plate containing acetosyringone (200 μM) and glucose (10 gm/l). Onto this filter was placed one large clump of friable callus which was then gently broken up and dispensed evenly over the filter. About 500 μl of *Agrobacterium* suspension was pipetted evenly onto the callus. The plates were sealed with parafilm and placed in the dark at room temperature for three days.

Selection and regeneration of transformants: Subsequent to the three day co-cultivation, the co-cultivated calli were rinsed with 250 μg/ml cefotaxime solution to suppress bacterial growth, and the calli were placed on MMSG medium containing 200 μg/ml hygromycin and 250 μg/ml cefotaxime. The calli were kept in the dark at room temperature for 6–8 weeks and checked periodically for proliferation of the calli on hygromycin. The hygromycin-resistant calli were moved to new MMSG plates with hygromycin and kept in the dark at room temperature until well proliferated. Then a portion of the hygromycin-resistant callus was tested for GUS activity to ensure that transformation had occurred.

Portions of the putatively transformed calli were then moved to Regeneration Medium I (MSO I) containing cefotaxime and hygromycin and were kept in the dark room at room temperature. After one week, they were moved to the light for regeneration. The tiny shoots were separated and transferred to deep petri plates containing Regeneration Medium II (MSO II) to promote root growth and hygromycin and cefotaxime to maintain respectively selection pressure and kill any remaining *Agrobacterium* cells.

REFERENCES

Aldemita, R. R. and T. K. Hodges (1996) *Agrobacterium tumefaciens*-mediated transformation of japonica and indica rice varieties. *Planta* 199:612–617.

Belanger, F. C., C. L. Laramore, and P. R. Day (1996) Turfgrass biotechnology. *Rutgers Turfgrass Proceedings* 28:1–3.

Cheng, M., J. E. Fry, S. Pang, H. Zhou, C. M. Hironaka, D. R. Duncan, T. W. Conner and Y. Wan (1997) Genetic transformation of wheat mediated by *Agrobacterium tumefaciens*. *Plant Physiology* 115:971–980.

Czernilofsky, A. P., R. Hain, L. Herrera-Estrella, H. Lorz, E. Goyvaerls, B. J. Baker and J. Schell (1986) Fate of selectable marker DNA integrated into the genome of *Nicotiana tabacum*. *DNA* 5:101–113.

Hiei, Y., S. Ohta, T. Komari and T. Kumashiro (1994) Efficient transformation of rice (*Oryza sativa* L.) mediated by *Agrobacterium* and sequence analysis of the boundaries of the T-DNA. *Plant Journal* 6:271–282.

Ishida, Y., H. Saito, S. Ohta, Y. Hiei, T. Komari and T. Kumashiro (1996) High efficiency transformation of maize (*Zea mays* L.) mediated by *Agrobacterium tumefaciens*. *Nature Biotechnology* 14:745–750.

Keller, T., H. G. Damude, D. Werner, P. Doerner, R. A. Dixon and C. Lamb (1998) A plant homolog of the neutrophil NADPH oxidase gp91$^{phox}$ subunit gene encodes a plasma membrane protein with $Ca^{2+}$ binding motifs. *Plant Cell* 10:255–266.

Knipple, D. C., C. L. Rosenfield, S. J. Miller, W. Liu, J. Tang, P. W. K. Ma and W. L. Roelofs (1998) Cloning and functional expression of a cDNA encoding a pheromone gland-specific acyl-CoA $\Delta^{11}$-desaturase of the cabbage looper moth, *Trichoplusia ni*. *Proc. Natl. Acad. Sci. USA* 95:15287–15292.

Komari, T. (1990) Transformation of cultured cells of *Chenopodium quinoa* by binary vectors that carry a fragment of DNA for the virulence region of pTiB0542. *Plant Cell Rep.* 9:303–306.

Komari, T., Y. Hiei, Y. Saito, N. Murai, and T. Kumashiro (1996) Vectors carrying two separate T-DNAs for co-transformation of higher plants mediated by *Agrobacte-* rium tumefaciens and segregation of transformants free from selection markers. *Plant J.* 10: 165–174.

Lee, L. (1996) Turfgrass biotechnology. *Plant Science* 115: 1–8.

Lodge, J., W. K. Kaniewski and N. E. Tumer (1993) Broad spectrum virus resistance in transgenic plants expressing pokeweed antiviral proteins. *Proc. Natl. Acad. Sci. USA* 90: 7089–7093.

Manuel de la Fuente, J., V. Ramires-Rodriquez, J. L. Cabrera-Ponce and L. Herrera-Estrella (1997) Aluminum tolerance in transgenic plants by alteration of citrate synthesis. *Science* 276:1566–1568.

May, G. D., R. Afza, H. S. Mason, A. Wiecko, F. J. Novak and C. J. Arntun (1995) Generation of transgenic banana (*Musa acuminata*) plants via *Agrobacterium*-mediated transformation. *Biotechnology* 13:486–492.

Meesters, P. A. E. P., J. Springer and G. Eggink (1997) Cloning and expression of the Δ-9 fatty acid desaturase gene from *Cryptococcus curvatus* ATCC 20509 containing histidine boxes and a cytochrome $b_5$ domain. *Appl. Microbiol. Biotechnol.* 47:663–667.

Mittler, R., V. Shulaev and E. Lam (1995) Coordinated activation of programmed cell death and defense mechanisms in transgenic tobacco plants expressing a bacterial proton pump. *Plant Cell* 7: 29–42.

Saito, Y. T. Komari, C. Matsuta, Y. Hayashi, T. Kumashiro and Y. Takanami (1992) Cucumber mosaic virus-tolerant transgenic tomato plants expressing satellite RNA. *Theor. App. Genet.* 83: 679–683.

Stukey, J. E., V. M. Mc Donough and C. E. Martin (1990) The ole1 gene of *Saccharomyces cerevisiae* encodes the Δ-9 fatty acid desaturase and can be functionally replaced by the rat stearoyl-CoA desaturase gene. *J. Biol. Chem.* 265:20144–20149.

Tingay, S., D. McElroy, R. Kalla, S. Fieg, M. Wang, S. Thornton and R. Brettell (1997) *Agrobacterium tumefaciens*-mediated barley transformation. *Plant Journal* 11:1369–1376.

Wang, C., C.-K. Chin and A. Chen (1998) Expression of the yeast delta nine desaturase gene in tomato enhances its resistance to powdery mildew. *Physiological and Molecular Plant Pathology* 38:255–263.

Wu, G., B. J. Shortt, E. B. Lawrence, E. B. Levine, K. C. Fitzsimmons and D. M. Shah (1995) Disease resistance conferred by expression of a gene encoding $H_2O_2$-generating glucose oxidase in transgenic potato plants. *Plant Cell* 7:1357–1368.

Yuan, R. (1998) Biotech driving innovations in rice cultivation. *Genetic Engineering News*, Jan. 15 issue: 13–32.

Zoubenko, O., F. Uckun, Y. Hur, I. Chet and N. Tumer (1997) Plant resistance to fungal infection induced by nontoxic pokeweed antiviral protein mutants. *Nature Biotech.* 15: 992–996.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

The invention claimed is:

1. A method of producing a transgenic turfgrass plant, comprising the steps of:

(a) culturing embryogenic tissue from seeds of a turfgrass plant on a medium that promotes de-differentiation of the tissue, to produce regenerable callus tissue;

(b) inoculating the callus tissue with *Agrobacterium* carrying at least one vector for transformation, the vector comprising virB, virG and virG virulence genes from plasmid pSB1 or pSB4, in which vector is inserted a heterologous DNA construct and a selectable marker conferring antibiotic resistance to transformed cells, wherein the DNA construct and selectable marker are operably linked to a promoter from a monocotyledonous species, wherein the inoculating comprises mixing the callus tissue with the *Agrobacterium* pre-incubated with acetosyringone, under conditions permitting the *Agrobacterium* to infiltrate the callus tissue, thereby forming *Agrobacterium*-infiltrated callus tissue;

(c) co-culturing the *Agrobacterium*-infiltrated callus tissue under conditions that enable the *Agrobacterium* vector to transform cells of the *Agrobacterium*-infiltrated callus tissue;

(d) selecting transformed cells by culturing the *Agrobacterium*-infiltrated callus tissue on a selection medium comprising an antibiotic, wherein the transformed cells are resistant to the antibiotic and are selected by their growth in the presence of the antibiotic; and (e) regenerating a transformed turfgrass plant from the transformed cells.

2. The method of claim 1, wherein the turfgrass is a species selected from the group consisting of creeping bentgrass, tall fescue, velvet bentgrass, perennial ryegrass, hard fescue, Chewings fescue, strong creeping fescue, colonial bentgrass and Kentucky bluegrass.

3. The method of claim 1, wherein the promoter is selected from the group consisting of maize ubiquitin gene promoters, rice actin gene promoters, maize Adh 1 gene promoters, rice or maize tubulin (Tub A, B or C) gene promoters, and alfalfa His 3 gene promoters.

4. The method of claim 1, wherein the selectable marker gene confers hygromycin resistance on transformed cells.

5. The method of claim 1, wherein the vector comprises a transgene selected from the group consisting of:

(a) a gene encoding glucose oxidase;

(b) a gene encoding citrate synthase;

(c) a gene encoding Δ-9 desaturase from *Saccharomyces cerevisiae* or *Cryptococcus curvatus*;

(d) a gene encoding Δ-11 desaturase;

(e) a gene encoding a plant homolog of the neutrophil NADPH oxidase;

(f) a gene encoding bacteriopsin from *Halobacterium halobium*; and (g) a gene encoding pokeweed antiviral protein.

* * * * *